US009916653B2

(12) United States Patent
Lin

(10) Patent No.: US 9,916,653 B2
(45) Date of Patent: Mar. 13, 2018

(54) DETECTION OF DEFECTS EMBEDDED IN NOISE FOR INSPECTION IN SEMICONDUCTOR MANUFACTURING

(75) Inventor: Jason Z. Lin, Saratoga, CA (US)

(73) Assignee: KLA-Tenor Corporation, Milpitas, CA (US)

( * ) Notice: Subject to any disclaimer, the term of this patent is extended or adjusted under 35 U.S.C. 154(b) by 1397 days.

(21) Appl. No.: 13/534,899

(22) Filed: Jun. 27, 2012

(65) Prior Publication Data

US 2014/0002632 A1 Jan. 2, 2014

(51) Int. Cl.
G06K 9/46 (2006.01)
H04N 7/18 (2006.01)
G06T 7/00 (2017.01)
G01N 21/88 (2006.01)
G01N 21/956 (2006.01)

(52) U.S. Cl.
CPC ......... *G06T 7/001* (2013.01); *G01N 21/8851* (2013.01); *G01N 21/95607* (2013.01); *G01N 2021/8887* (2013.01); *G01N 2021/95615* (2013.01); *G06T 2207/20076* (2013.01); *G06T 2207/20081* (2013.01); *G06T 2207/30148* (2013.01)

(58) Field of Classification Search
CPC .......... H04N 7/18; G06K 9/46; G06T 7/0002; G06T 2207/20021; G06T 7/001; G06T 7/0004; G06T 2207/30148
USPC ............................................. 348/87; 382/149
See application file for complete search history.

(56) References Cited

U.S. PATENT DOCUMENTS 7,127,099 B2 * 10/2006 Noy ................. G01N 21/95607
356/237.1
7,330,581 B2 * 2/2008 Ishikawa ................. G06T 7/001
382/145
7,440,607 B1 * 10/2008 Lin ..................... G01N 21/8851
382/149

(Continued)

FOREIGN PATENT DOCUMENTS

TW 201113515 A 4/2011
TW 201128183 A 8/2011

OTHER PUBLICATIONS

PCT International Search Report and Written Opinion of the International Searching Authority for Application No. PCT/US2013/047909, dated Sep. 30, 2013 (Sep. 30, 2013), 8 sheets.

*Primary Examiner* — Deirdre Beasley
(74) *Attorney, Agent, or Firm* — Okamoto & Benedicto LLP

(57) ABSTRACT

One embodiment relates to an apparatus for detecting defects on a manufactured substrate. The apparatus includes an imaging tool arranged to obtain image frames from the manufactured substrate. The apparatus further includes a data processing system which includes computer-readable code configured to compute features for pixels in an image frame and divide the pixels in the image frame into feature-defined groups of pixels. The computer-readable code is further configured to select a feature-defined group, and generate a multi-dimensional feature distribution for the selected feature-defined group. Another embodiment relates to a method of detecting defects from a test images frame and multiple reference image frames. Other embodiments, aspects, and features are also disclosed.

16 Claims, 5 Drawing Sheets

(56) References Cited

U.S. PATENT DOCUMENTS

| | | | | |
|---|---|---|---|---|
| 7,848,563 B2* | 12/2010 | Sakai | G06T 7/001 382/144 |
| 8,537,349 B2* | 9/2013 | Huet | G01R 31/2656 356/237.2 |
| 8,664,596 B2* | 3/2014 | Zhao | G01N 23/225 250/306 |
| 2002/0181760 A1* | 12/2002 | Asai | G01N 21/95692 382/149 |
| 2006/0066843 A1* | 3/2006 | Guetta | G01N 21/9501 356/237.2 |
| 2008/0205747 A1* | 8/2008 | Kuchii | G06T 5/20 382/149 |
| 2008/0297783 A1* | 12/2008 | Urano | G01N 21/9501 356/237.5 |
| 2009/0080759 A1* | 3/2009 | Bhaskar | G06T 7/001 382/141 |
| 2009/0238445 A1* | 9/2009 | Yang | G06T 7/0004 382/149 |
| 2010/0053319 A1* | 3/2010 | Sakai | G06T 7/001 348/125 |
| 2011/0182496 A1* | 7/2011 | Sakai | G01N 21/956 382/145 |
| 2011/0310241 A1* | 12/2011 | Postolov | G01N 21/9501 348/87 |
| 2012/0114220 A1* | 5/2012 | Srocka | G01N 21/95 382/144 |
| 2012/0141012 A1* | 6/2012 | Sakai | G01N 21/9501 382/149 |
| 2012/0185818 A1* | 7/2012 | Leu | G03F 1/84 716/136 |
| 2012/0229618 A1* | 9/2012 | Urano | G01N 21/9501 348/92 |
| 2013/0294680 A1* | 11/2013 | Harada | H01L 22/20 382/149 |

\* cited by examiner

FIG. 1      100

DETECTION OF DEFECTS EMBEDDED IN NOISE FOR INSPECTION IN SEMICONDUCTOR MANUFACTURING

BACKGROUND

Technical Field

The present invention relates generally to wafer and reticle inspection apparatus and methods of using same.

Description of the Background Art

Automated inspection and review systems are important in process control and yield management for the semiconductor and related microelectronics industries. Such systems include optical and electron beam (e-beam) based systems.

In the manufacture of semiconductor devices, detection of defects early on in the development and fabrication process is becoming increasingly important to shorten product development cycles and increase manufacturing yield. Advanced wafer and reticle inspection systems are being used to detect, review and classify defects and feed the root cause information back into the manufacturing process to prevent these defects going forward. The size of relevant defects is directly proportional to the design rule being applied to the manufacturing of the semiconductor devices. As the design rule being applied continues to shrink, the performance demands on inspection systems increases both in terms of imaging resolution and speed (defects processed per hour).

SUMMARY

One embodiment relates to a method of detecting defects from a test images frame and multiple reference image frames. Features for pixels in the test and reference image frames are computed, and the pixels in said image frames are divided into feature-defined groups of pixels. A feature-defined group is selected, and a multi-dimensional feature distribution is generated for the selected feature-defined group.

In addition, a normal cluster in the multi-dimensional feature distribution may be determined, and outlier points which are outside the normal cluster may be detected. Defective pixels associated with the outlier points may be located, and the defective pixels may be flagged and/or reported.

One embodiment relates to an apparatus for detecting defects on a manufactured substrate. The apparatus includes an imaging tool arranged to obtain image frames from the manufactured substrate. The apparatus further includes a data processing system which includes computer-readable code configured to perform a method of detecting defects which divides pixels into feature-defined groups and generates group-specific feature distributions in order to detect outlier points.

Other embodiments, aspects, and features are also disclosed.

DETAILED DESCRIPTION

Figure 1:
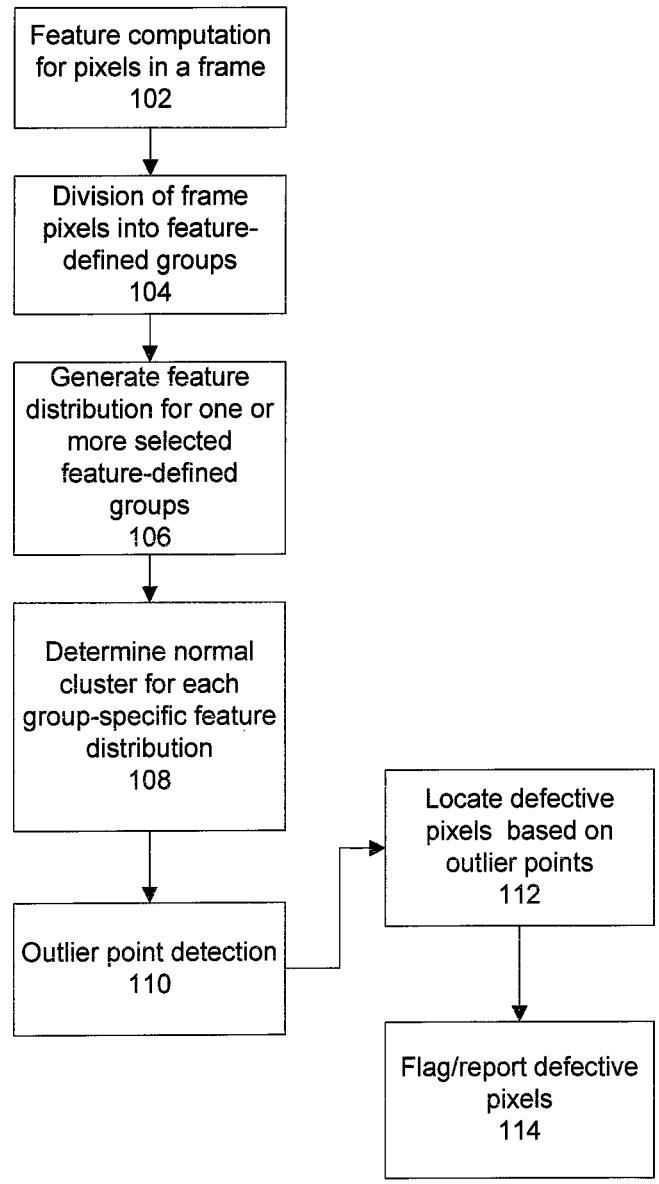
FIG. 1 is a flow chart depicting a method of detecting defects in image data in accordance with an embodiment of the invention.

According to an embodiment of the present invention, images from at least two dice may be used to perform the defect detection. The image associated with the die in which defects are to be detected may be referred to as the test image, and the images associated with other dice may be referred to as the reference images.

The present application discloses an innovative technique to improve sensitivity of defect detection during the inspection of manufactured semiconductor substrates. In particular, the technique improves the sensitivity of detecting defects which may be "embedded in noise" in a feature distribution plot (multi-dimensional signal) over a multi-dimensional feature space.

To form the feature distribution plot, each point in the multi-dimensional feature space may be assigned with a population value. For example, if there are one hundred pixels in the frame area having identical test and reference features, the population value of the feature point is assigned as one hundred.

In the technique disclosed previously in U.S. Pat. No. 7,440,607, the feature distribution plot is preferably formed based on the features of the pixels within the area of a frame, as derived from the test image and the multiple reference images. Because the values of the multiple features of non-defective (normal) pixels fall within certain nominal ranges, a normal cluster (normal distribution) is generally formed by the feature distribution of non-defective pixels in the feature distribution plot. Defective pixels become outliers in the feature distribution plot because one or more of their feature values do not fall in the nominal ranges.

In order to improve the defect detection, more features may be used in generating the feature distribution plot. However, applicant has determined that, when more than two dimensions are used, the normal cluster (normal distribution) formed by the non-defective pixels in the feature distribution plot often becomes sparse, making it difficult to separate outliers from the normal cluster.

In contrast, in accordance with an embodiment of the present invention, pixels of a frame are divided into separate feature-defined groups based on one or more reference features. Subsequently, one of the groups of pixels may be selected, and the feature distribution plot may be formed based on the test and reference features of pixels within the selected group (without including pixels outside the group).

Applicant has determined that this technique is advantageous in that it allows for the detection of defects which are not detected previously. This is because the previously un-detected defects were embedded in the "noise" around the normal cluster based upon all pixels in a frame. In contrast, these defects become detectable outliers when the normal cluster is based upon pixels in a selected feature-defined group. This is because when a separate distribution plot is created for a separate group of pixels, the noise attributable to the non-selected groups is effectively removed from the plot.

FIG. 1 is a flow chart depicting a method 100 of detecting defects in image data in accordance with an embodiment of the invention. The image data may include a test image and corresponding reference images. The reference and test images may be each divided into a number of frames. Each frame may cover a significant number of pixels in a local area of a die. The frame may be rectangular or square. For instance, 512×512 or 1024×1024 pixels may form a square frame.

Feature Computation

The first step 102 of the method 100 involves the computation of reference features and test features for pixels in reference and test images. The reference and test features may be determined as follows.

A reference feature may be defined as some property associated with a same (corresponding) pixel location on multiple reference images. For example, the reference feature may be the average or median of gray levels across multiple reference dice at the same pixel location. As another example, a reference feature may be the range or deviation of the gray levels across multiple reference dice at the pixel location.

A reference feature derived from a pixel location may also include the information around the pixel location. For example, the local range or local average of a three-pixel-wide-by-three-pixel-high area centered at the pixel location (or other local area defined relative to the pixel location) on each reference image may be calculated first, and then these local ranges or averages may be used to derive the reference feature of the pixel location. For instance, a median of local averages across multiple dice may be one of the reference features of the pixel location. Many other features may be derived according to these principles.

A test feature may be derived from a pixel location on the test image as well as the multiple reference images. One example of a test feature is the difference between the gray level on the test image and the average of the gray levels on the reference images. Another example of a test feature is the difference between the gray level on the test image and the median of the gray levels on the reference images. Similar to a reference feature, a test feature derived from a pixel location may also include the information around the pixel location. For example, a local average around a three-pixel-wide-by-three-pixel-high area centered at the pixel location (or other local area defined relative to the pixel location) on the test image may be used for computing the difference to the average of the local averages around a three-pixel-wide-by-three-pixel-high area of the corresponding location on the multiple reference images.

Feature-Defined Grouping and Group-Specific Feature Distributions

In the second step 104, the pixels of a frame may be divided into feature-defined groups. In this step, at least one feature is used to separate at least one group of pixels from other pixels in the inspected area. For example, pixels of a densely patterned area typically have more local gray level range variation than pixels in an open area. Therefore, a local gray level range may be used as a feature for dividing pixels into different population groups.

In the third step 106, a multi-dimensional feature distribution may be generated for one or more selected groups of pixels. In contrast, a previous technique would use all pixels of an image frame to generate a multi-dimensional feature distribution to be used for outlier detection.

Figure 2:
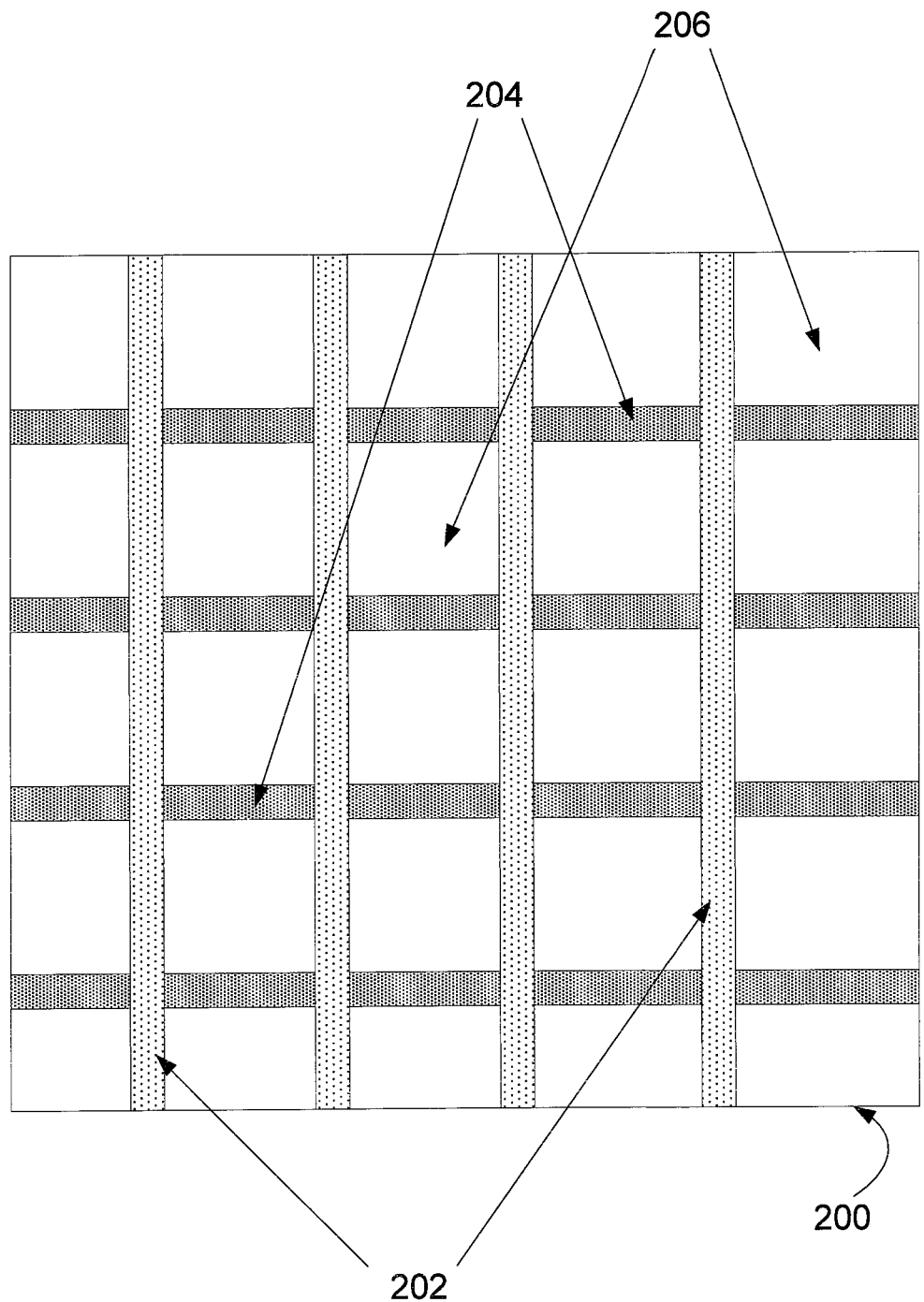
FIG. 2 is a diagram depicting an example inspected area within an image frame in accordance with an embodiment of the invention.

For example, consider the inspected area as shown in the image frame 200 depicted in FIG. 2. As shown, the image frame 200 includes vertical lines 202, horizontal line segments 204, and open spaces 206.

A previous technique would use all pixels in the frame 200 to generate a multi-dimensional feature distribution. In contrast, the presently-disclosed technique first divides the pixels in the frame 200 into groups based on a computed feature per the second step 104.

In a first example, using a local gray level range or other computed feature, the pixels of the frame 200 may be separated into a first group including the pixels of both the vertical lines 202 and horizontal line segments 204, and a second group including the pixels of the open spaces 206. In a second example, the pixels of the frame 200 may be separated into a first group including the pixels of the vertical lines 202, a second group including the horizontal line segments 204, and a third group including the pixels of the open spaces 206.

Subsequently, per the third step 106, one or more of the feature-defined groups may be selected, and a multi-dimensional feature distribution may be generated separately for each of the selected groups.

Normal Cluster Determination

The fourth step 108 of the method 100 may determine the pixels that fall into the normal cluster (normal distribution) of points for each group-specific feature distribution. In accordance with embodiments of the present invention, there may be several valid approaches for defining the normal cluster of pixels.

One approach to identify the normal distribution is based on the population in the local neighborhood of a point location of the signal distribution formed in the multi-dimensional feature space. For a two-dimensional example, a pre-defined population density threshold for the total population of points within, for example, a five-pixel-wide-by-five-pixel-high square area centered on a given point in the two-dimensional signal distribution may be used as a threshold to determine if the given point is normal or not. If the population value is greater than the population density threshold, the point may be considered to be normal.

Another approach for identifying the normal distribution is based on the connectedness among points in the signal distribution. For a two-dimensional example, a point may be considered normal if, in the signal distribution, there are other points within a pre-defined distance.

Other approaches may also be used to define the normal distribution. As an example, a point may be considered normal if it satisfies both criteria described above. In principle, if there are a considerable number of pixels that have identical or similar features, they are considered normal and not defective.

Outlier Detection

The fifth step 110 may identify the pixels that are statistical outliers, which may be indicative of defects on the test substrate. As described above, the normal cluster of points in the group-specific feature distribution has been identified. Every point that is not identified as within the normal cluster may be considered as a candidate point. A candidate point may contain one or more pixels that correspond to one or more real defects.

In order to allow some margin for error, a tolerance range may be allowed before a point is declared defective. There may be different approaches in defining the tolerance range. One approach is a fixed tolerance range. In a two dimensional example, the tolerance range may be a pre-defined distance from a normal point to the candidate point. If the candidate point is disposed at a greater distant from any normal point than the pre-defined distance, it may be declared a defective point in that pixels associated with the candidate point may be deemed to be defective. More complex rules such as making the pre-defined distance a function of the reference features may also be added in defining the tolerance range. As an example, the distance may be a function of a reference feature that is defined as the average gray level across multiple reference dice.

To achieve optimal performance in identifying real defects and eliminating nuisances, parameters such as the tolerance range are tuned. Each defective point may be viewed in the multi-dimensional feature space, and the tolerance range may be tuned to capture points corresponding to defects of interest, while the points corresponding to nuisances are eliminated.

Defective Pixel Identification

As described above, outlier points may be detected in a group-specific feature distribution during the fifth step 110, and pixels associated with the outlier points may be deemed to be defective. It is noted that in the multi-dimensional feature space, each point represents one or more pixels that have certain feature characteristics. However, the actual pixel locations where the pixels are in the frame area may not be directly retained in the feature distribution. Therefore, it may be necessary to perform additional processing to locate these defective pixels per the sixth step 112.

Once the defective pixels associated with the outlier points have been located, these defective pixels may be flagged and reported per the seventh step 114. In one embodiment, the report may be made to the tool operator and/or to an engineering database, so that an investigation of the defects may be made. In some embodiments, the tool in which the present method of defect detection is implemented also includes methods for defect analysis and identification. In other embodiments, the two functions of detection and analysis are separately implemented.

Example Feature Distribution Plots

Figure 3:
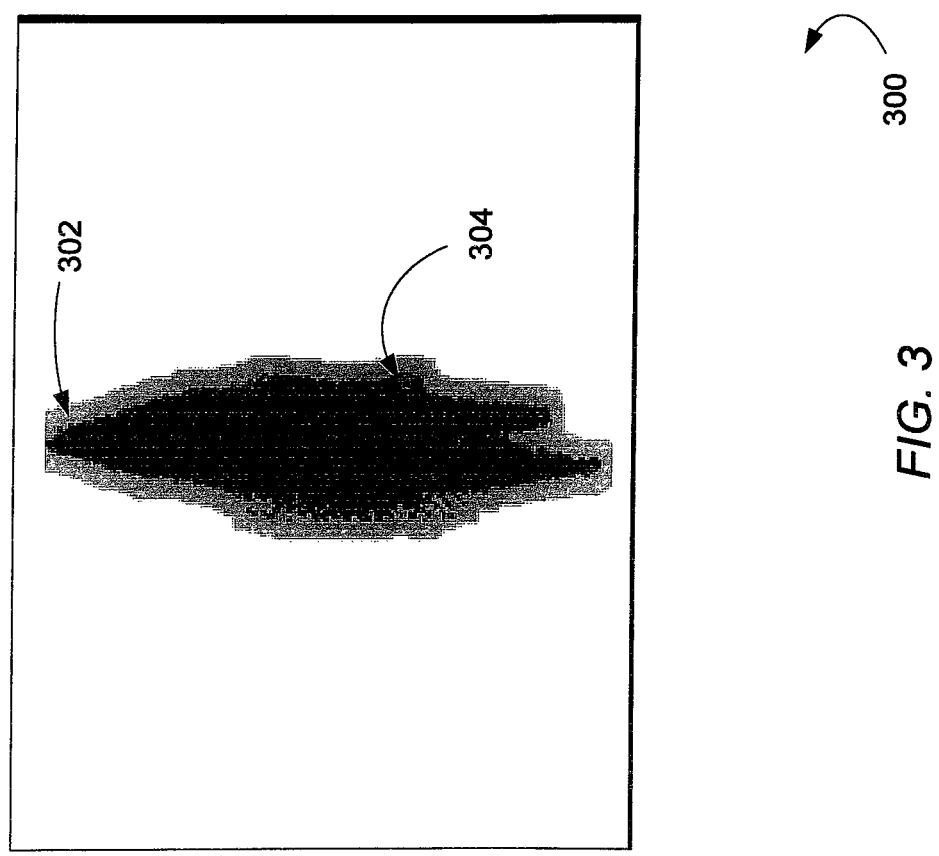
FIGS. 3 and 4 show example two-dimensional feature distribution plots which are generated from an image frame of an inspected area that is similar to the framed area depicted in FIG. 2
Figure 4:
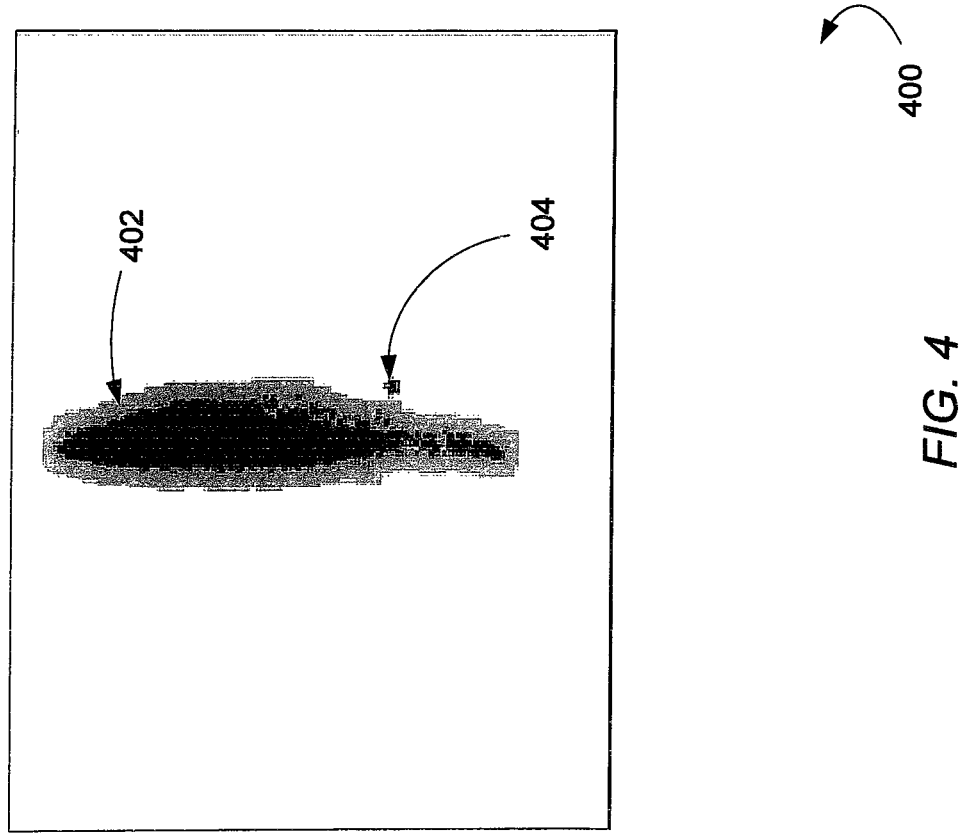

FIGS. 3 and 4 show example two-dimensional feature distribution plots which are generated from an image frame of an inspected area that is similar to the framed area 200 depicted in FIG. 2 in that it has vertical lines 202, horizontal line segments 204, and open areas 206. A darker point in the plots indicates a greater population of pixels with feature values in the ranges associated with that point.

The feature distribution plot 300 in FIG. 3 is generated from all pixels in the image frame 200. The normal cluster 302 is clearly visible in the plot. In this case, there is a point 304 which has associated with it pixels which are actually defective. However, in this feature distribution 300, the point 304 falls within the "noise" near the edge of the normal cluster 302. Hence, the point 304 is not identifiable as an outlier in this distribution.

In contrast, the feature distribution plot 400 in FIG. 4 is generated from only pixels of the vertical lines 202 in the image frame 200. The normal cluster 402 is again clearly visible in the plot. The normal cluster 402 in FIG. 4 is substantially smaller (tighter) than the normal cluster 302 in FIG. 3. In this case, the point 404 which has associated with it pixels which are actually defective is outside the normal cluster 402. Hence, in this feature distribution 400, the point 404 is identifiable as an outlier.

High-Level Diagram of Apparatus

Figure 5:
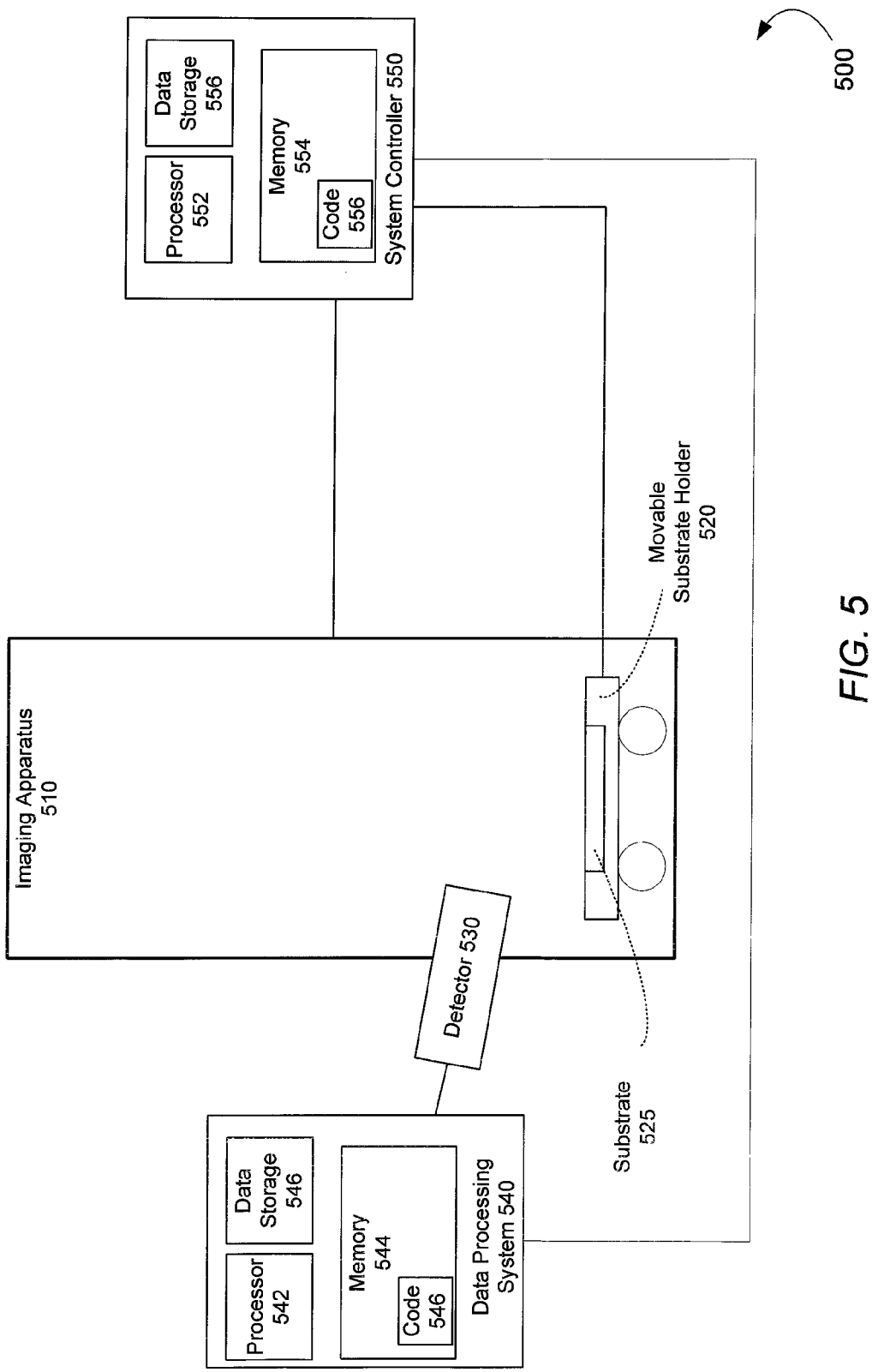
FIG. 5 is a schematic diagram of an inspection apparatus that may be utilized for automatically inspecting manufactured substrates in accordance with an embodiment of the invention.

FIG. 5 is a schematic diagram of an inspection apparatus that may be utilized for inspection of manufactured substrates in accordance with an embodiment of the invention. As shown in FIG. 5, the inspection apparatus includes an imaging tool 510, a movable substrate holder 520, a detector 530, a data processing system 540, and a system controller 550.

In one embodiment, the imaging tool 310 comprises an electron beam (e-beam) imaging column. In an alternate embodiment, the imaging tool 510 comprises an optical imaging apparatus. In accordance with an embodiment of the invention, the imaging tool 510 includes electronics to control and adjust the magnification of the imaging.

The movable substrate holder 520 may comprise a translatable mechanism to hold a target substrate 525. The target substrate 525 may be, for example, a semiconductor wafer or a reticle for lithography. The detector 530 is an appropriate detector for the particular imaging apparatus, and the data processing system 540 is configured to process image data from the detector 530. The data processing system 540 may also include a processor 542, memory 544 for holding computer-readable code 545, a data storage system 548 for storing data, and various other components, such as a system bus, input/output interfaces, and so forth.

The system controller 550 may be communicatively coupled to the imaging tool 510 so as to electronically control the operation of the imaging tool 510. The system controller 550 may also include a processor 552, memory 554 for holding computer-readable code 555, a data storage system 556 for storing data, and various other components, such as a system bus, input/output interfaces, and so forth.

CONCLUSION

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc.

In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. An apparatus for detecting defects on a manufactured substrate, the apparatus comprising:
    an imaging tool arranged to obtain image frames from the manufactured substrate; and
    a data processing system including a processor, memory and computer-readable code in said memory, the computer-readable code being configured to
    compute features for pixels in an image frame;
    separate pixels in the image frame that have values of the features within specified ranges of values from other pixels in the image frame such that the separated pixels form a feature-defined group of pixels;
    generate a multi-dimensional feature distribution for only the pixels in the image frame belonging to the feature-defined group of pixels;
    determine a normal cluster in the multi-dimensional feature distribution; and
    detect outlier points in the multi-dimensional feature distribution which are outside the normal cluster.

2. The apparatus of claim 1, wherein the computer-readable code is further configured to locate defective pixels associated with the outlier points.

3. The apparatus of claim 2, wherein the computer-readable code is further configured to report the defective pixels.

4. The apparatus of claim 1, wherein the features include reference features, and wherein a reference feature is a property associated with a pixel location on multiple reference images.

5. The apparatus of claim 4, wherein the features further include test features, and wherein a test feature is derived from a pixel location on a test image and the multiple reference images.

6. The apparatus of claim 4, wherein the property comprises a range of gray levels at the pixel location.

7. The apparatus of claim 4, wherein the property includes information from a local range of pixels centered at the pixel location.

8. A method of detecting defects from a test image frame and multiple reference image frames, the method comprising:
    imaging, by an imaging apparatus, a local area of a manufactured substrate held on a movable substrate holder to generate the test image frame; and
    using a data processing system including a processor, memory and computer-readable code in said memory to perform steps including:
        computing features for pixels in the test image frame and the multiple reference image frames;
        separate pixels in the image frame that have values of the features within specified ranges of values from other pixels in the image frame such that the separated pixels form a feature-defined group of pixels;
        generating a multi-dimensional feature distribution for only the pixels belonging to the feature-defined group of pixels;
        determining a normal cluster in the multi-dimensional feature distribution; and
        detecting outlier points in the multi-dimensional feature distribution which are outside the normal cluster.

9. The method of claim 8 further comprising:
locating defective pixels associated with the outlier points.

10. The method of claim 9 further comprising:
flagging the defective pixels.

11. The method of claim 8, wherein the features include reference features, and wherein a reference feature is a property associated with a pixel location on the multiple reference image frames.

12. The method of claim 11, wherein the features further include test features, and wherein a test feature is derived from a pixel location on a test image frame and the multiple reference image frames.

13. The method of claim 11, wherein the property comprises a range of gray levels at the pixel location.

14. The method of claim 11, wherein the property includes information from a local range of pixels centered at the pixel location.

15. A non-transitory tangible data storage medium storing computer-readable code configured to perform a method comprising:
    computing features for pixels in the test and reference image frames;
    using the features computed for the pixels in the test image frame and the multiple reference image frames to separate pixels belonging to a feature-defined group of pixels from other pixels that do not belong to the feature-defined group of pixels;
    generating a multi-dimensional feature distribution for only the pixels belonging to the feature-defined group of pixels;
    determining a normal cluster in the multi-dimensional feature distribution; and
    detecting outlier points in the multi-dimensional feature distribution which are outside the normal cluster.

16. The non-transitory tangible data storage medium of claim 15, wherein the method further comprises:
    locating defective pixels associated with the outlier points; and
    flagging the defective pixels.

* * * * *